(12) United States Patent
López Ordaz

(10) Patent No.: US 6,660,227 B2
(45) Date of Patent: Dec. 9, 2003

(54) DEVICE AND METHOD FOR DETECTING, ISOLATING AND ELIMINATING HAZARDOUS MICROBIOLOGICAL POLLUTING AGENTS

(75) Inventor: Oscar Raúl López Ordaz, Monterrey (MX)

(73) Assignee: Innovatek Corporation, Monterrey (MX)

( * ) Notice: Subject to any disclaimer, the term of this patent is extended or adjusted under 35 U.S.C. 154(b) by 0 days.

(21) Appl. No.: 10/065,151

(22) Filed: Sep. 20, 2002

(65) Prior Publication Data

US 2003/0021723 A1 Jan. 30, 2003

(51) Int. Cl.[7] .......................... A61L 2/00; G01N 21/00; A61G 11/00; F26B 3/34; B07C 5/00
(52) U.S. Cl. .................... 422/24; 422/1; 422/4; 422/40; 422/120; 422/186; 422/292; 422/305; 250/453.11; 250/455.11; 312/1; 34/275; 209/584; 209/578; 209/DIG. 10; 294/55

(58) Field of Search ............................. 422/1, 4–5, 24, 422/40, 120, 186, 292, 305–307; 250/453.11, 455.11; 312/1; 34/275; 209/584, 578, DIG. 900; 294/55

(56) References Cited

U.S. PATENT DOCUMENTS 4,059,903 A * 11/1977 Piet et al.
5,316,733 A * 5/1994 Rune et al.

FOREIGN PATENT DOCUMENTS

WO     WO 0038742     9/2000

\* cited by examiner

Primary Examiner—Robert J. Warden, Sr.
Assistant Examiner—Monzer R. Chrobaji
(74) Attorney, Agent, or Firm—Jay R. Yablon

(57) ABSTRACT

A device for detecting, isolating and exterminating hazardous microbiological agents contained inside delicate objects such as envelopes and packages commonly used in worldwide mail and transport systems which may be safely used in houses, is very economic and which can be easily produced.

27 Claims, 2 Drawing Sheets

DEVICE AND METHOD FOR DETECTING, ISOLATING AND ELIMINATING HAZARDOUS MICROBIOLOGICAL POLLUTING AGENTS

BACKGROUND OF INVENTION

The present invention relates to devices for exterminating polluting microbiological agents and more particularly to a device for detecting, isolating and exterminating hazardous microbiological agents contained inside objects such as envelopes and packages commonly used in worldwide mail and transport systems.

In the last year it has been noted that some terrorists use the worldwide mail system for sending terrorist attacks by enclosing anthrax spores (normally as anthrax powder) inside envelopes and packages.

The anthrax infects humans by inhalation, contact or ingestion of polluted products with the *Bacillus antracis* spore which is very resistant and may survive even for decades in dark and dry places and which occurs naturally in wild and domestic animals such as calf, goats, camels, antelopes and other herbivores that may infect humans by contact with infected animals or tissues coming from infected animals.

Once the anthrax spores enter the organism, they may be attacked by antibiotics, however, the antibiotics have a limited effect once the toxins generated by the spore are liberated in the organism. According to specialists, If the toxin concentration is very high, the patient may pass away, even though all spores have been eliminated.

Due to the high resistance of the anthrax spore, to its capacity for surviving large periods of time and to its high volatility—as anthrax powder—this organism has been chose by terrorist organizations for performing terrorist attacks using the worldwide mail and courier systems.

The anthrax infection by contact, inhalation and/or ingestion, may occur as follow: once the envelope or package arrives to its destination and someone opens the envelope or package, the spores "jump" out and remain suspended in the air for a while until an air current disseminate the spore or until they are adsorbed by a person through the nasal fossae into the lunges, where the spores begin to produce toxins which may be lethal. Other spores may fall on the skin, which produces the most benign of the anthrax infections. Other spores may fall on food which may produce a infection by ingestion when the aliments are consumed.

It has to be understood that the three kinds of infection do not necessarily occur at the same time, since only one kind of infection may occur.

One method for eliminating anthrax spores without opening the envelope is by controlled radiations such as x-rays which are harmful for any living organism, however, the use of controlled radiations emission apparatuses is restricted for domestic use due to its dangerousness.

An apparatus for eliminating pathogen microorganisms such as Salmonella, *E. Coli,* hepatitis, AIDS and anthrax by infrared radiations is claimed in patent application No. WO/0038742 B1 of Ingemanson, which include infrared radiation emission means.

Although Ingemanson's apparatus may be effective for eliminating almost all pathogen microorganisms, due to its inherent sterilization method by infrared radiations—heat—it is not suitable for paper articles, which may become fragile or even burnt. Furthermore, Ingemanson's apparatus is quite expensive.

Therefore, there is a need for an economical and secure device for domestic use, which may be used not only for the sterilization of envelopes and packages, but for detecting the presence of the anthrax spore inside envelopes and packages.

It is therefore a main object of the present invention to provide a device for detecting, isolating and eliminating any kind of bacteriologic agent contained inside any object, specially envelopes and packages.

It is another main object of the present invention, to provide a device of the above referred nature which may be safely used in houses, is very economic and which can be easily produced.

These and other objects and advantages of the device and method for detecting, isolating and eliminating hazardous microbiological polluting agents of the present invention will become apparent to those persons having an ordinary skill in the art, from the following description of the invention.

SUMMARY OF INVENTION

In order to satisfy the above-referred needs, applicant developed a domestic apparatus for detecting, isolating and eliminating any kind of polluting bacteriologic agent such as anthrax spores.

The apparatus developed by applicant comprise in its more general embodiment: a hollow container divided in a transparent inspection section and a sterilization section, wherein the transparent inspection section has an aperture including access means which may be withdrawn or placed in a closed position on said aperture, thus completely sealing the aperture; means for manipulating the object inside the inspection and sterilization sections; particle collector means, attached inside the transparent inspection section; and sterilization means, located in the sterilization section for exterminating any bacteriologic agent.

Thanks to the fact that the objects are manipulated inside a sealed container, the possibility of an infection by anthrax or other microbiological agent is eliminated.

Moreover, thanks to the particle collector means, it can be properly detected any trace of particles which may be bacteriological agents.

In case that any particle is detected on the particle collector means, the radiation emission means must be activated in order to eliminate any kind of polluting microbiological agent that may be isolated inside the container, and public health authorities must be contacted.

The device developed by applicant may be used in houses and is very economic, its operation is very safe and can be easily produced.

Furthermore, applicant developed a method for detecting, isolating and eliminating polluting microbiological agents.

The method developed by applicant, in its most general embodiment, comprise the following steps: providing a device comprising a hollow container divided in a transparent inspection section and a sterilization section, wherein the transparent inspection section has an aperture including access means which may be withdrawn or placed in a closed position on said aperture, thus completely sealing the aperture; means for manipulating the object inside the inspection and sterilization sections; particle collector means, attached inside the transparent inspection section; and sterilization means, located in the sterilization section for exterminating any bacteriologic agent; introducing an object inside the transparent inspection section; shaking the object using the means for manipulating objects over the particle collector means; and seeking for any particle traces on the particle collector means; if any traces of particles are detected inside the inspection section then the next steps must be carried out: introducing the object and the particle collector means inside the sterilization section; and activating the sterilization means.

Thanks to the method developed by applicant, it can be detected, isolated and eliminated any kind of microbiological agent contained in any object including envelopes and packages, eliminating the possibility of an infection by a polluting microbiological agent such as anthrax.

BRIEF DESCRIPTION OF DRAWINGS

The features of the invention believed to be novel are set forth in the appended claims. The invention, however, together with further objects and advantages thereof, may best be understood by reference to the following description taken in conjunction with the accompanying drawing(s) in which:

DETAILED DESCRIPTION

Figure 1:
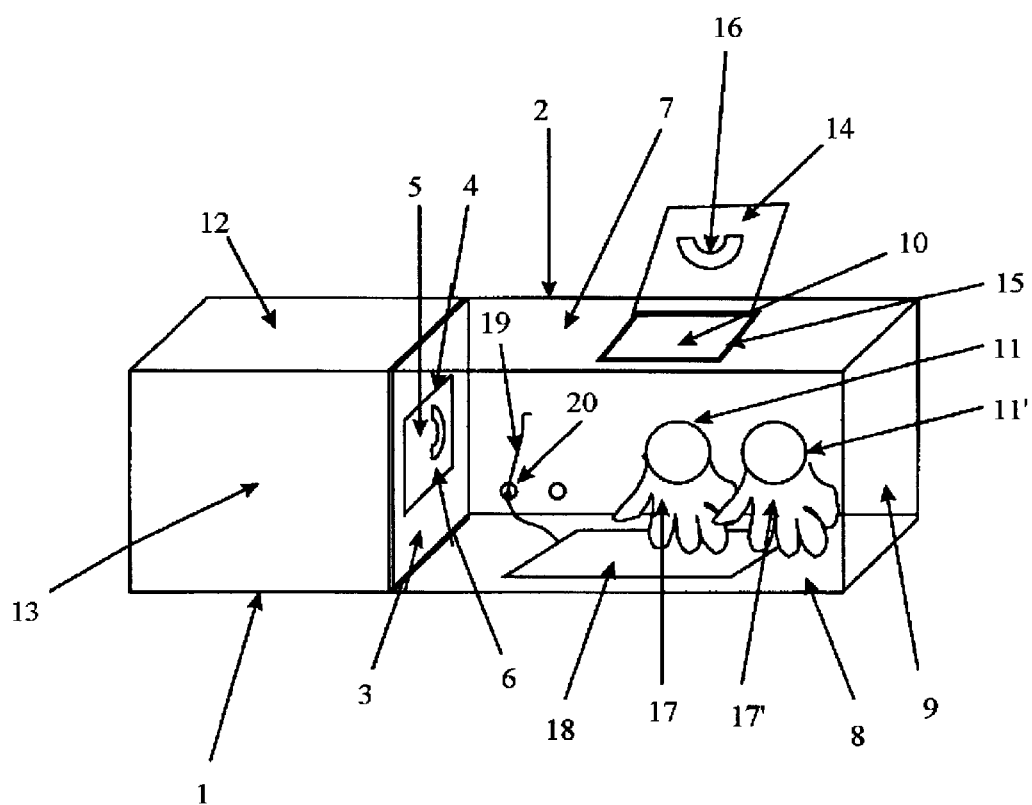
FIG. 1 is a view in perspective of the device for detecting, isolating and eliminating hazardous microbiological polluting agents of the present invention.
Figure 2:
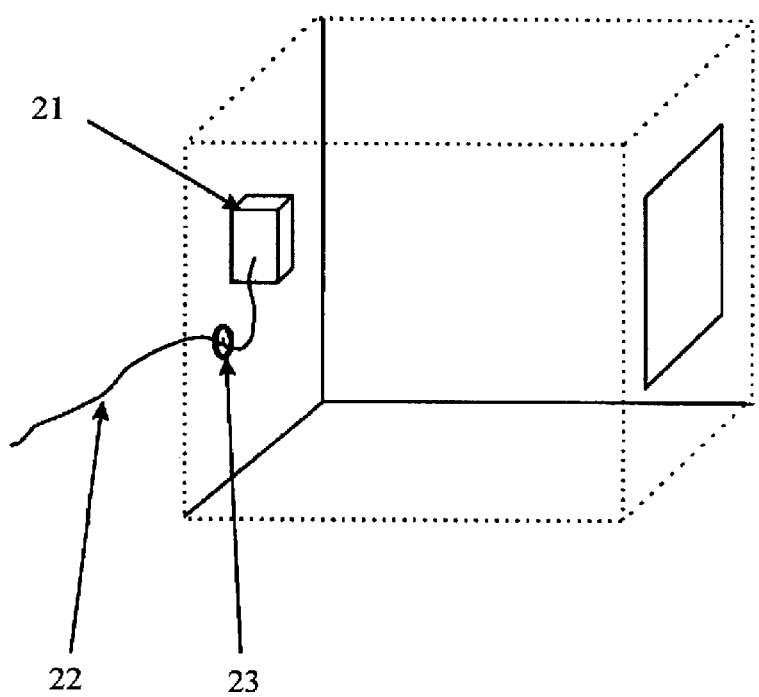
FIG. 2 is a perspective view of the sterilization section showing its interior.

The device for detecting, isolating and eliminating hazardous microbiological polluting agents of the present invention, will be described referring to a preferred embodiment thereof, which is illustrated in the accompanying drawings wherein the same signs and numbers refer to the same parts of the figure shown, the device of the present invention comprising:

a rectangular acrylic container divided in two sections: an opaque section 1 having an interior protective layer which avoids the pass of x-rays to the outside of the container, and a transparent section 2, wherein both sections are divided by an opaque divisional wall 3 having a protective layer that avoids the pass of UV rays to the transparent section 2 of the container, said wall having a rectangular aperture 4 including an access door 5 having an UV ray protective layer including a handle 6 facing the transparent section 2;

wherein the transparent section 2 includes a superior 7 and inferior 8 transparent walls, a transparent lateral wall 9 opposed to the opaque divisional wall 3, a first and a second transparent longitudinal walls, each wall having an interior and an exterior surface (not shown), said superior wall 7 having a quadrangular aperture 10 and said first longitudinal wall having a first and a second lined up circular apertures 11, 11' in a close relationship;

wherein the opaque section 1 includes a superior 12 and inferior (not shown) opaque walls, a lateral opaque wall (not shown) opposed to the opaque divisional wall and a first 13 and a second (not shown) opaque longitudinal walls;

wherein the quadrangular aperture 10 of the transparent section superior wall 7 has a quadrangular transparent access door 14 fitting the quadrangular aperture 10, including a peripheral rubber seal 15 completely closing and sealing the quadrangular aperture 10 and including a handle 16 for opening or closing the access door;

wherein each circular aperture 11, 11' located in the first longitudinal wall is sealed by a latex glove 17, 17' joined by the periphery of its hand access to the periphery of a circular aperture in the first longitudinal wall exterior surface in such way that the glove 17, 17' remains inside the container;

wherein the internal surface of the inferior wall 8 has an electrostatic charge generator metal plaque 18 attached by a plurality of bolts (not shown) to said internal surface and connected to an electric source (not shown) by a cable 19 exiting the transparent section 2 of the container through an aperture 20 located at the first longitudinal wall including a rubber seal (not shown), for attracting and retaining any particle having a size of 1 micron or more which may be present inside the container transparent section 2, said plaque 18 including removable means for retaining particles once the electrostatic charge dissipates comprising a plastic plaque covered with an adhesive substance (not shown), which entirely covers the metal plaque 18 ; and wherein the opaque section 1 include means for emitting UV radiations 21 to the interior of the opaque section 1, attached to the lateral wall and connected to an external energy source by a cable 22 exiting the opaque section 1 through an aperture 23 located in the lateral wall and having an UV radiation resistant rubber seal (not shown)

The user introduces the object to be inspected into the transparent section 2 through the transparent access door 14. Once the object is isolated inside the transparent section 2, it can be manipulated by hand using the integrated gloves 17, 17'.

When the superior wall transparent access door 14 is sealing the quadrangular aperture 10, both sections of the container are completely sealed and no particle can enter or exit the device.

The user introduces the object to be inspected into the transparent section 2 trough the transparent access door 14. Once the object is isolated inside the transparent section 2, it can be manipulated by hand using the integrated gloves 17, 17'.

In case the object being inspected is, for example, an envelope, the user may open the envelope and shake it over the plastic strip of the electrostatic charge generator metal plaque 18 so that any bacteriologic content is attracted by the plaque 18 and adhered on the plastic strip.

Any harmful materials that remain suspended inside the container will be attracted by the metal plaque 18, achieving that the interior of the container be free of any particles.

Even though there wasn't any visible material falling form the object, if the plastic strip appears covered by dust or any other material, the object and plastic strip must be introduced into the opaque section 1 through the opaque divisional wall access door 5. Once the object (or objects) and the plastic strip are inside the opaque section 1, the opaque divisional wall access door 5 must be closed and the UV radiation emitting means 21 activated by means of a switch (not shown) located at the opaque section second longitudinal wall, in order to kill any bacteriological agent that may be present inside the opaque section 1 of the container. Once the sterilization has been carried out, the container must remain sealed and the public health authorities must be contacted for adequately retiring and analyzing the remaining material.

Even though there weren't any trace of dust or material in the plastic strip, the objects and the plastic strip may be introduced in the opaque section 1 for sterilization with UV radiations for a complete protection against any germ or harmful material.

Although in the preferred embodiment of the invention it was described the use of UV radiation emission means 21, it may be used means for emitting any kind of radiation authorized for domestic use or means for vaporizing a bactericide substance.

And although it has been described the use of an electrostatic charge generator metal plaque 18 for attracting and retaining particles, it must be understood that it can be used any kind of particle attracting and retaining means, such as a fan for attracting particles to a paper or plastic strip covered with an adhesive substance.

Furthermore, the transparent access door 14 may be substituted by any other access means, provided that they completely seal the access to the container.

Finally, the container may include means for detecting and notifying the presence of bacteriological agents inside the container or on the particle attracting and retaining means.

The method for detecting, isolating and eliminating microbiological agents of the present invention will be described in accordance with a preferred embodiment thereof, wherein the method of the present invention comprises the steps of:

providing a container divided in two connected sections: a transparent section and an opaque section having an anti UV radiations protective layer, said container including: an opaque divisional wall covered with anti UV layer having an opaque access door, an access door located at the transparent section which completely seal the container when its in a closed position, removable particle collector means comprising an electrostatic generator metal plaque having a removable plastic strip covered with an adhesive substance and completely covering the plaque, two latex gloves passing through two apertures located at the transparent section and completely sealing said apertures and UV radiation emission means located inside the opaque section;

introducing an envelope or package inside the transparent section through the access door;

manipulating the envelope or package by hand using the latex gloves and open it;

shaking the envelope over the particle collector means;

seeking for particle traces on the plastic strip which may have been attracted by the electrostatic charge;

if any traces of particles are found, then the following steps must be carried out:

manipulating the envelope and its content, and

Introduce them to the opaque section through the opaque access door;

retiring the plastic strip and introduce it in the opaque section; and activating the UV radiations emission means in order to kill any bacteriological agent that may be present in the envelope or package.

If, after shaking the envelope or package on the particle collector means, no trace of particles or any material can be detected on the plastic strip, the envelope or package can be retired from the transparent section of the container.

Although it was described that only one envelope or package is inspected inside the container, it may be inspected a plurality of envelopes, packages or any other objects depending of the size of the container.

Finally it must be understood that the device and method for detecting, isolating and eliminating hazardous microbiological polluting agents of he present invention, are not limited exclusively to the above described and illustrated embodiments and that the persons having ordinary skill in the art can, with the teaching provided by this invention, make modifications to the device and method of the present invention, which will clearly be within the true inventive concept and scope of the invention which is claimed in the following claims.

While only certain preferred features of the invention have been illustrated and described, many modifications and changes will occur to those skilled in the art. It is, therefore, to be understood that the appended claims are intended to cover all such modifications and changes as fall within the true spirit of the invention.

What is claimed is:

1. A device for detecting, isolating and eliminating microbiological polluting agents contained in any object, comprising:

a hollow container divided in a transparent inspection section and a sterilization section, wherein the transparent inspection section has an aperture including access means which may be opened or placed in a closed position on said aperture, thus completely sealing the aperture;

means for manipulating the object inside the inspection and sterilization sections;

particle collector means, attached inside the transparent inspection section; and sterilization means, located in the sterilization section for exterminating any bacteriologic agent.

2. A device as claimed in claim 1 wherein the hollow container comprises a rectangular box divided in an inspection section and a sterilization section by a divisional wall having an access door for communicating both sections.

3. A device as claimed in claim 1, wherein the hollow container comprises a rectangular box divided in an inspection section and a sterilization section by a divisional wall having an access door for communicating both sections, said access door having an open and a closed position, which in the closed position, completely isolates both sections from each other.

4. A device as claimed in claim 1, wherein the hollow container comprises a rectangular box divided in an inspection section and a sterilization section by a divisional wall, said inspection section including an upper and a lower transparent wall, a transparent lateral wall opposed to the divisional wall, and a first and a second longitudinal transparent wall, each of the transparent walls having an internal and an external surface, said superior wall having a quadrangular aperture including an access door having an open and a closed position which in the closed position, completely seals the quadrangular aperture.

5. A device as claimed in claim 1, wherein the hollow container comprises a rectangular box divided in an inspection section and a sterilization section by a divisional wall, said inspection section including an upper and a lower transparent wall, a transparent lateral wall opposed to the divisional wall, and a first and a second longitudinal transparent wall, each of the transparent walls having an internal and an external surface, wherein the first longitudinal wall has two lined up circular apertures each having a peripheral portion and wherein the means for manipulating objects inside the inspection and sterilization sections comprise two latex gloves, each joined to the peripheral portion of a circular aperture in such way that each glove completely seals the circular apertures and remains inside the container thus allowing the introduction of a gloved hand inside the container.

6. A device as claimed in claim 1, wherein the particle collector means attract and retain particles having a particle size of between about 1 to 300 microns.

7. A device as claimed in claim 1, wherein the hollow container comprises a rectangular box divided in an inspection section and a sterilization section by a divisional wall, said inspection section including an upper and a lower transparent wall, a transparent lateral wall opposed to the divisional wall, and a first and a second longitudinal transparent wall, each of the transparent walls having an internal and an external surface, wherein the particle collector means is attached to the internal surface of the inspection section.

8. A device as claimed in claim 1, wherein the particle collector means, comprise an electrostatic charge generator metal plaque connected to an electric source including removable particle retaining means for retaining particles once the electrostatic charge dissipates, comprising a plastic plaque covered with an adhesive substance, which entirely covers the metal plaque.

9. A device as claimed in claim 1, wherein the hollow container comprises a rectangular box divided in an inspection section and a sterilization section by a divisional wall, said inspection section including an upper and a lower transparent wall, a transparent lateral wall opposed to the divisional wall, and a first and a second longitudinal transparent wall, each of the transparent walls having an internal and an external surface, wherein the particle collector means comprise an electrostatic charge generator metal plaque attached to the internal surface of the lower transparent wall.

10. A device as claimed in claim 1, wherein the particle collector means comprise a plastic strip covered with an adherent substance.

11. A device as claimed in claim 1, wherein the hollow container comprises a rectangular box divided in an inspection section and a sterilization section by a divisional wall, said inspection section including an upper and a lower transparent wall, a transparent lateral wall opposed to the divisional wall, and a first and a second longitudinal transparent wall and said inspection section including an upper and a lower opaque walls, an opaque lateral wall opposed to the divisional wall, and a first and a second longitudinal opaque wall each having an internal and an external surface having a protective layer that avoids the pass of radiations, and wherein the sterilization means comprises radiation emission means for exterminating any microbiological agent.

12. A device as claimed in claim 1, wherein the hollow container comprises a rectangular box divided in an inspection section and a sterilization section by a divisional wall, said inspection section including an upper and a lower transparent wall, a transparent lateral wall opposed to the divisional wall, and a first and a second longitudinal transparent wall, and said inspection section including an upper and a lower opaque walls, an opaque lateral wall opposed to the divisional wall, and a first and a second longitudinal opaque wall each having an internal and an external surface having a protective layer that avoids the pass of UV rays, and wherein the sterilization means comprises radiation emission means located inside the sterilization section and attached to the internal surface of the upper wall.

13. A device as claimed in claim 1, wherein the hollow container comprises a rectangular box divided in an inspection section and a sterilization section by a divisional wall, said inspection section including an upper and a lower transparent wall, a transparent lateral wall opposed to the divisional wall, and a first and a second longitudinal transparent wall, and said inspection section including an upper and a lower opaque walls, an opaque lateral wall opposed to the divisional wall, and a first and a second longitudinal opaque wall each having an internal and an external surface having a protective layer that avoids the pass of UV rays, and wherein the sterilization means comprises UV radiation emission means for exterminating any microbiological agent.

14. A device as claimed in claim 1, wherein the hollow container comprises a rectangular box divided in an inspection section and a sterilization section by a divisional wall, said inspection section including a superior and an inferior transparent wall, a transparent lateral wall opposed to the divisional wall, and a first and a second longitudinal transparent wall, and said inspection section including a superior and an inferior opaque walls, an opaque lateral wall opposed to the divisional wall, and a first and a second longitudinal opaque wall each having an internal and an external surface having a protective layer that avoids the pass of UV rays, and wherein the sterilization means comprises UV radiation emission means connected to an energy source by a conductor cable exiting the opaque section through an aperture located in the lateral wall and having an UV radiation resistant rubber seal.

15. A device as claimed in claim 1, wherein the sterilization means comprising means for vaporizing a bactericide substance inside the sterilization section.

16. A device as claimed in claim 1, additionally including means for detecting and informing the presence of microbiological agents inside the hollow container or on the particle collector means, which generates an alarm signal if microbiological agents are detected.

17. A method for detecting, isolating and eliminating hazardous microbiological polluting agents contained in any object comprising:
   providing a device comprising a hollow container divided in a transparent inspection section and a sterilization section, wherein the transparent inspection sect an aperture including access means which may be opened or placed in a closed position on said aperture, thus completely sealing the aperture; means for manipulating the object inside the inspection and sterilization sections; particle collector means, attached inside the transparent inspection section; and sterilization means, located in the sterilization section for exterminating any bacteriologic agent;
   introducing an object inside the transparent inspection section;
   shaking the object using the means for manipulating objects over the particle collector means; and
   looking for any particle traces on the particle collector means.

18. A method as claimed in claim 17, further including the following steps if any said particle traces are seen inside the inspection section:
   introducing the object and the particle collector means inside the sterilization section; and
   activating the sterilization means.

19. The method as claimed in claim 17, wherein the device further including means for detecting and informing the presence of microbiological agents inside the hollow container or on the particle collector means, which generates an alarm signal if microbiological agents are detected.

20. The method as claimed in claim 17, wherein the means for manipulating objects inside the container comprising two latex gloves passing through one wall of the inspection section of the container and completely sealing the container.

21. The method as claimed in claim 17, wherein the particle collector means comprising an electrostatic charge generator metal plaque located inside the inspection section.

22. The method as claimed in claim 17, wherein the particle collector means comprising a removable plastic strip covered with an adherent substance.

23. The method as claimed in claim 17, wherein the sterilization means comprising radiation emission means located inside the sterilization section.

24. The method as claimed in claim 17, wherein the sterilization means comprising UV radiation emission means located inside the sterilization section.

25. The method as claimed in claim 17, wherein the sterilization means comprising means for vaporizing a bactericide substance inside the sterilization section.

26. A method for detecting, isolating and eliminating hazardous microbiological polluting agents contained in envelopes or packages comprising the steps of:

providing a container divided in two connected sections: a transparent section and an opaque section having an anti UV radiations protective layer, said container including: an opaque divisional wall covered with anti UV layer having an opaque access door, an access door located in the transparent section which completely seal the container when its in a closed position, removable particle collector means comprising an electrostatic generator metal plaque having a removable plastic strip covered with an adhesive substance and completely covering the plaque, two latex gloves passing through two apertures located at the transparent section and completely sealing said apertures and UV radiation emission means located inside the opaque section;

introducing an envelope or package inside the transparent section through the access door;

opening the envelope or package by hand using the latex gloves;

shaking the envelope over the particle collector means; and looking for particle traces on the plastic strip which may have been attracted by the electrostatic charge.

27. The method as claimed in claim 26, further comprising the following steps if any said particle traces are seen inside the inspection section:

manipulating the envelope and its content, and introduce them to the opaque section through the opaque access door;

removing the plastic strip and introducing it in the opaque section; and activating the UV radiations emission means in order to kill any bacteriological agent that may be present in the envelope or package.

\* \* \* \* \*